United States Patent [19]
Wise, Jr. et al.

[11] Patent Number: 5,148,040
[45] Date of Patent: Sep. 15, 1992

[54] RADIATION BLOCKING DEVICE AND METHOD OF USE WITH RADIATION DETECTING PROBE

[75] Inventors: Robin A. Wise, Jr., Morgan Hill, Calif.; Robert G. Carroll, Largo, Fla.

[73] Assignee: Care Wise Medical Products Corp., Morgan Hill, Calif.

[21] Appl. No.: 728,509

[22] Filed: Jul. 11, 1991

[51] Int. Cl.$^5$ ............................................. G21F 3/00
[52] U.S. Cl. ................................................ 250/515.1
[58] Field of Search ............ 250/515.1, 518.1, 519.1; 378/203, 145; 600/1, 3; 128/653.1

[56] References Cited

U.S. PATENT DOCUMENTS

| | | |
|---|---|---|
| 3,723,743 | 3/1973 | Brackenbrough et al. ...... 250/515.1 |
| 4,801,803 | 1/1989 | Denen et al. |
| 4,946,435 | 8/1990 | Suthanthiran et al. ................ 600/3 |
| 4,959,547 | 9/1990 | Carroll et al. ..................... 250/505.1 |
| 5,036,201 | 7/1991 | Carroll et al. ..................... 250/505.1 |

Primary Examiner—Jack I. Berman
Assistant Examiner—Kiet T. Nguyen
Attorney, Agent, or Firm—Caesar, Rivise, Bernstein, Cohen & Pokotilow, Ltd.

[57] ABSTRACT

A shield for use with a radiation detecting probe to effect the detection, localization, imaging or mapping of radiation in a first portion of the body of a living being by use of a hand held, radiation detecting probe. The probe has a conical field of view. The shield comprises a sheet formed of a radiation blocking material, e.g., pure tungsten, tungsten alloys, tungsten powder suspended in gold, pure gold, gold alloys, pure platinum, and platinum-iridium alloys, and is sized to be readily located within a space within the body of the being so that the first portion of the body of the being is interposed between it and the probe, with the shield filling up a substantial portion of the field of view of the probe. In one embodiment the shield is mounted on the probe by an adjustable yoke assembly. In another embodiment the shield is separate from the probe.

21 Claims, 1 Drawing Sheet

U.S. Patent  Sep. 15, 1992  5,148,040
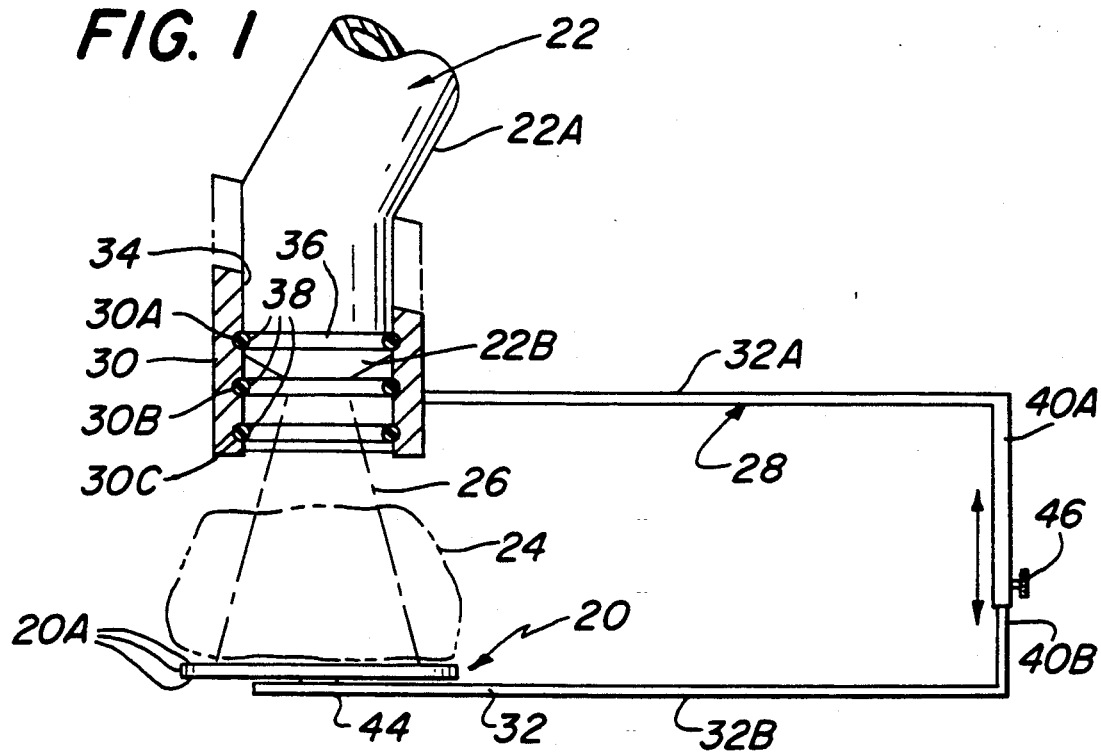
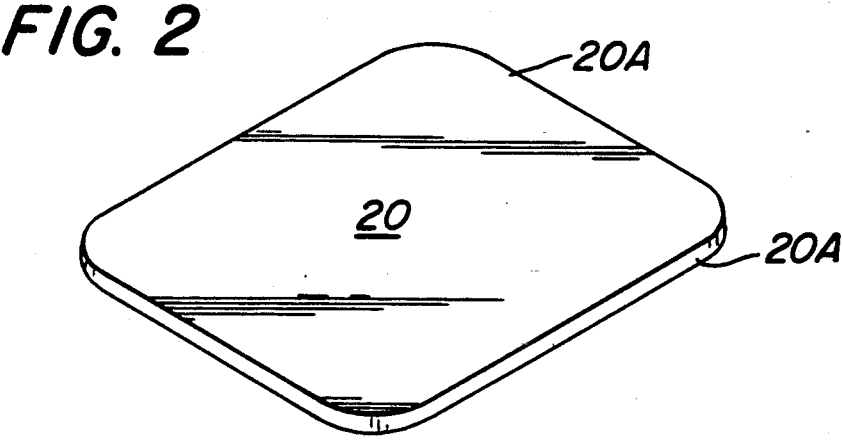

RADIATION BLOCKING DEVICE AND METHOD OF USE WITH RADIATION DETECTING PROBE

BACKGROUND OF THE INVENTION

This invention relates generally to detecting radiation in a living being for medical applications, and more particularly to detecting, localizing, and imaging or mapping of radiation in a portion of the body of a being by means of a radiation detecting probe and an associated radiation blocking shield.

The use of radioactive materials to tag tissue within a patient for effecting its localization and demarcation by radiation detecting devices has been disclosed in the medical literature for at least forty years. Significant developments in the localization and demarcation of tissue bearing radioactive isotope tags for diagnostic and/or therapeutic purposes have occurred since that time.

Thus, it is now becoming an established modality in the diagnosis and/or treatment of certain diseases, e.g., cancer, to introduce monoclonal antibodies tagged with a radioactive isotope (e.g., Indium 111, Technetium 99m, Iodine 123, and Iodine 125) into the body of the patient. Such monoclonal antibodies tend to seek out particular tissue, such as the cancerous tissue, so that the gamma radiation emitted by the isotope can be detected by a hand-held radiation detecting probe. Such a probe is disposed or held adjacent portion of the patient's body where the cancerous tissue is suspected to be in order to detect if any radiation is emanating from that site, thereby indicating that cancerous tissue is likely to be found there.

Prior art, hand-held, radiation detecting probes are commercially a available from the assignee of this invention, Care Wise Medical Products, Inc. under the trademark OncoProbe.

In copending U.S. patent applications Ser. Nos. 07/363,243 and 07/491,390, filed on Jun. 8, 1989 and Mar. 9, 1990, respectively, and assigned to the same assignee as this invention there are disclosed hand-held radiation detecting probes having collimating means to establish the field of view of the probe. In U.S. Pat. No. 4,801,803 (Denen et al) there is also disclosed a hand-held radiation detecting probe.

In some cases background activity (i.e., radiation emanating from portions of the body other than the portion being investigated) may interfere with sensitive and accurate surgical radiation detecting probe localization of radiolabeled tissues within body cavities.

OBJECTS OF THE INVENTION

It is a general object of this invention to provide simple means and a method of use for minimizing the problem of background activity interference with sensitive and accurate localization of radiolabeled tissues within body cavities.

It is a further object of this invention to provide a means for use with a radiation detecting probe to block background radiation emanating from sources other than the tissue being examined by the probe within the probe's field of view.

It is still a further object of this invention to provide means which may be readily inserted into the body of a being interposed between the tissues being examined by a radiation detecting probe and the remainder of the body cavity in the field of view of the probe.

It is yet a further object of this invention to provide a radiation blocking shield which is simple in construction and easy to use.

SUMMARY OF THE INVENTION

These and other objects of this invention are achieved by providing a shield for use with a radiation detecting probe to effect the detection, localization, imaging or mapping of radiation in a first, internal, portion of the body of a living being by use of the probe.

The shield comprises a sheet formed of a radiation blocking material which is sized to be readily located within a space within the body of the being so that the first portion of the body of the being is interposed between it and the probe, whereupon the shield fills up a substantial portion of the field of view of the probe, thereby blocking radiation from sources behind the shield.

In one embodiment the shield is mounted on the probe by an adjustable yoke assembly. In another embodiment the shield is separate from the probe.

DESCRIPTION OF THE DRAWINGS

Other objects and many attendant features of this invention will become readily appreciated as the same becomes better understood by reference to the following detailed description when considered in connection with the accompanying drawings wherein:

FIG. 1 is a side elevational view, partially in section, of one embodiment of the radiation shield of the subject invention; and FIG. 2 is a perspective view of a second embodiment of the radiation shield of the subject invention.

DETAILED DESCRIPTION OF THE PREFERRED EMBODIMENTS

Referring now to various figures of the drawing wherein like reference numerals refer to like parts there is shown at 20 in FIGS. 1 and 2 a radiation blocking shield constructed in accordance with this invention and arranged to be used with any type of radiation detecting probe 22. In accordance with a preferred embodiment of this invention the probe 22 is a small, hand-held unit like any of the types disclosed in the aforementioned patent applications of the assignee of this invention, although other probes can also be used.

The probe 22, being a small, hand-held unit, is particularly suitable for use in the operating room to assist the surgeon in detecting and localizing the presence of radioactively tagged tissue 24 within the body of the patient. The probe consists of a cylindrical radiation shielding body, radiation detection means (not shown) located within the body, and collimating means (not shown) to establish the conical (solid angle of acceptance) field of view (shown by the broken lines designated by the reference numeral 26 in FIG. 1).

The probe's body 22 has a proximal portion 22A of a generally cylindrical shape and size to be readily held in one's hand. The body portion 22A terminates in a distal portion or tip 22B extending at an acute angle, e.g., 60 degrees, to the longitudinal axis of the body portion. The angular orientation of the tip with respect to the hand grip portion 22A of the probe's body facilitates operator comfort and ease of aiming.

In use the probe 22 is arranged to detect the presence of radiation within its field of view, and to provide electrical output signals indicative thereof, via a cable or wiring harness (not shown), to a conventional analyzer (not shown) or other conventional monitoring or imaging apparatus (not shown) so that the location of the source of radiation may be determined. Thus, the probe 22 is held adjacent to a portion of the patient's body usually exposed during surgical operations where the cancerous tissue is suspected to be in order to detect if any radiation is emanating from that site, thereby indicating that cancerous tissue is likely to be found there.

As will be appreciated by those skilled in the art, radiation from the tagged tissue scatters off of the various surrounding body tissues or organs, thereby rendering the localization of the source of the radiation difficult. More importantly, current radiolabelled monoclonal antibodies also localize non selectively in liver and kidneys, providing intense background activity near tumor sites. The probe 22 provides significant shielding for radiation from all directions other than that within its field of view 26 by virtue of the materials used and the shape and organization of the probe. Thus, the probe 22 can be used with high energy radioisotopes, such as Indium 111, to expedite the localization procedure. As will be appreciated by those skilled in the art Indium 111 has approximately ten times the energy of Iodine 125 (e.g., 247 KEV versus 25-30 kev). Without good shielding and collimation the use of such high energy materials would be precluded for use in some applications, e.g., detecting tagged cancerous tissue located near the liver, kidneys, or blood vessels, any of which locations would include significant accumulations of the isotope on a non-specific basis.

The use of shield 20 with the probe 22 provides a significant aid in the localization procedure since it serves to shield the probe from radiation emanating from sources within the probe's field of view 26 but located behind the tissue/organ 24 being examined by the probe.

The shield 20 basically comprises a relatively thin sheet or disk formed of any suitable radiation blocking material, e.g., a material selected from the group comprising pure tungsten, tungsten alloys, tungsten powder suspended in gold, pure gold, gold alloys, pure platinum, and platinum-iridium alloys. The shield 20 is arranged to be placed within a space, e.g., an incision, in the body of the patient which is located immediately behind the tissue or organ 24 being investigated by the probe 22 so that the tissue/organ is interposed between the shield and the probe as shown in FIG. 1.

The shield 20 is of a sufficient size, e.g., approximately 3 inches (7.62 cm) wide by 3.5 inches (8.89 cm) high, so that it completely covers the probe's field of view 26. By so doing any radiation from a source located behind the shield 20 will be blocked by it and thus prevented from reaching the probe.

The shield is configured so that it is of an appropriate thickness to provide good radiation blocking characteristics without taking up substantial space within the patient's body. To that end when the shield is formed of tungsten it is approximately ⅛ inch (0.32 cm) thick.

Inasmuch as the shield 20 is arranged to be located within the body of the patient, depending upon the material making up the shield, its entire exposed exterior surface 20A may be plated or coated to ensure that it is non-toxic. For example, when the shield is formed of tungsten, tungsten alloys, or tungsten powder suspended in gold, the shield is preferably chrome plated. Other suitable, non-toxic plating or coating materials may be used.

The embodiment of the invention shown in FIG. 1 the shield 20 is arranged to be mounted onto the probe 22, whereas the embodiment of the shield shown in FIG. 2 is arranged to be used without attachment to the probe.

The mounting of the shield 20 on the probe 22, as shown in FIG. 1 is effected by use of a mounting assembly 28. The assembly 28 basically comprises a mounting sleeve 30 and associated yoke 32. The sleeve 30 is a hollow tubular member having a central bore 34 configured to receive the distal end or tip 22B of the probe 22. The distal end 22B of the probe includes a window (not shown) through which the radiation within the field of view 26 may pass to the radiation detecting means in the probe's body. Each end of the central bore 34 of the sleeve is open so that radiation may pass through the lower end to the window unobstructed by the sleeve.

The yoke 32 basically comprises two leg sections 32A, 32B. Each leg section is an elongated member formed of any material suitable for disposition within the body of a living being. The leg section 32A projects radially outward from the sleeve 30 and is fixedly secured thereto. The outer end of the leg section 32A extends perpendicularly to the remainder of the section 32A and is in the form of an elongated tube 40A. The leg section 32B is constructed similar to leg section 32A, with its perpendicularly extending portion 40B telescopically disposed within the tube 40A. The leg section 32B includes a free end 44 at which the shield 20 is fixedly mounted. Accordingly, the spacing between the sleeve 30 and the shield 20 can be adjusted by sliding the portions 40A and 40B with respect to each other. A thumb screw 46 is provided at their interface to lock the leg sections together at the desired position.

As can be seen clearly in FIG. 1 shield 20 is fixedly mounted on the free end of the leg section 32B so that it is located opposite to the distal end of the probe tip and centered within the probe's field of view 26 when the sleeve is in place on the probe tip.

It should be pointed out at this juncture that the use of the means for establishing the adjustablity of the legs of the yoke is merely exemplary and thus other means may be employed. In fact, the yoke may be constructed so that it is not adjustable, i.e., the position of the shield with respect to the sleeve is fixed. Moreover other means than a sleeve may be used to mount the shield on the probe tip.

An annular recess or groove 36 is provided about the periphery of the distal end of the probe to cooperate with means forming a portion of the sleeve 30 to releasably mount the sleeve 30 thereon at selected longitudinal positions. This feature enables the shield to be quickly and easily located at various distances from the probe as may be required during the radiation localization procedure without requiring the adjustment of the thumbscrew 46 and associated telescoping leg sections 40A and 40B (in the case where the yoke is itself constructed to be adjustable).

The means for releasably mounting the sleeve 30 onto the probe tip 22B basically comprises a plurality of annular grooves 30A, 30B, and 30C which extend about the periphery of the bore 34. Each recess has disposed therein a respective resilient material, e.g., rubber, O-ring 38. The sleeve is mounted on the probe's tip 22B by inserting that tip within its bore so that the O-ring 38 in a desired one of the grooves 30A-30C is located opposite to the recess 36 in the probe's tip at the desired longitudinal position for the sleeve. Accordingly, the O-ring will snap-fit into that recess, thereby holding the sleeve 30 in place at that particular longitudinal position along the tip.

Without further elaboration the foregoing will so fully illustrate our invention that others may, by applying current or future knowledge, adopt the same for use under various conditions of service.

What we claim is:

1. A shield for use with a radiation detecting probe to effect the detection, localization, imaging or mapping of radiation in a first, internal portion of the body of a living being by use of a radiation detecting probe, said probe having a field of view, said shield comprising a sheet formed of a radiation blocking material and sized to be readily located within a space in the body of the being so that said first, internal portion is interposed between remainder said shield and said probe, with said shield filling up a substantial portion of the field of view, thereby blocking radiation from sources behind said shield.

2. The shield of claim 1 wherein the surface of said shield which comes into contact with any portion of the body of said being is non-toxic.

3. The shield of claim 2 wherein said shield is formed of a material in the group comprising pure tungsten, tungsten alloys, tungsten powder suspended in gold, pure gold, gold alloys, pure platinum, and platinum-iridium alloys.

4. The shield of claim 3 wherein said tungsten, tungsten alloys, and tungsten powder suspended in gold, when used to form said shield are chrome plated.

5. The shield of claim 1 wherein said sheet is approximately 3 inches (7.62 cm) wide by 3.5 inches (8.89 cm) high.

6. The shield of claim 5 wherein said material is tungsten and said sheet is approximately ⅛ inch (0.32 cm) thick.

7. The shield of claim 1 additionally comprising means to mount said shield on said probe.

8. The shield of claim 7 wherein said last mentioned means is adjustable to vary the spacing of said shield from said probe.

9. The shield of claim 8 wherein said sheet is approximately 3 inches (7.62 cm) wide by 3.5 inches (8.89 cm) high.

10. The shield of claim 9 wherein said material is tungsten and said sheet is approximately ⅛ inch (0.32 cm) thick.

11. The shield of claim 7 wherein said sheet is approximately 3 inches (7.62 cm) wide by 3.5 inches (8.89 cm) high.

12. The shield of claim 11 wherein said material is tungsten and said sheet is approximately ⅛ inch (0.32 cm) thick.

13. The shield of claim 7 wherein the surface of said shield which comes into contact with any portion of the body of said being is non-toxic.

14. The shield of claim 13 wherein said shield is formed of a material in the group comprising pure tungsten, tungsten alloys, tungsten powder suspended in gold, pure gold, gold alloys, pure platinum, and platinum-iridium alloys.

15. The shield of claim 14 wherein said tungsten, tungsten alloys, and tungsten powder suspended in gold, when used to form said shield are chrome plated.

16. The shield of claim 8 wherein the surface of said shield which comes into contact with any portion of the body of said being is non-toxic.

17. The shield of claim 16 wherein said shield is formed of a material in the group comprising pure tungsten, tungsten alloys, tungsten powder suspended in gold, pure gold, gold alloys, pure platinum, and platinum-iridium alloys.

18. The shield of claim 17 wherein said tungsten, tungsten alloys, and tungsten powder suspended in gold, when used to form said shield are chrome plated.

19. A method of effecting the detection, localization, imaging or mapping of radiation in a first, internal portion of the body of a living being by use of a radiation detecting probe, said probe having a field of view, said method comprising introducing a shield into the body of said being, said shield comprising a sheet formed of a radiation blocking material and sized to be readily located within a space in the body of the being so that said first, internal portion is interposed between said shield and said probe, with said shield filling up a substantial portion of the field of view, whereupon said shield blocks radiation from sources behind said shield.

20. The method of claim 19 wherein said shield is mounted on said probe.

21. The method of claim 20 wherein the position of said shield with respect to said probe is adjustable via means mounting the shield on the probe.

* * * * *